United States Patent [19]

Bellani

[11] Patent Number: 5,731,433
[45] Date of Patent: *Mar. 24, 1998

[54] PROCESS FOR THE PREPARATION OF RUFLOXACIN AND SALTS THEREOF

[75] Inventor: Pietro Bellani, Rho, Italy

[73] Assignee: Archimica Spa, Orriggio, Italy

[*] Notice: The term of this patent shall not extend beyond the expiration date of Pat. No. 5,703,233.

[21] Appl. No.: 632,426

[22] PCT Filed: Oct. 26, 1994

[86] PCT No.: PCT/EP94/03512

§ 371 Date: Apr. 24, 1996

§ 102(e) Date: Apr. 24, 1996

[87] PCT Pub. No.: WO95/11907

PCT Pub. Date: May 4, 1995

[30] Foreign Application Priority Data

Oct. 27, 1993 [IT] Italy ................ MI93A2286

[51] Int. Cl.$^6$ .............. C07D 513/00; C07D 279/08; C07D 279/02; C07D 279/14
[52] U.S. Cl. .............. 544/32; 544/362; 544/363
[58] Field of Search ............... 544/32, 362, 363

[56] References Cited

U.S. PATENT DOCUMENTS 4,772,605  9/1988  Naik et al. ................ 514/254

FOREIGN PATENT DOCUMENTS 522 277 A1  1/1993  European Pat. Off. .
0100992  1/1989  Japan .
2217710  11/1989  United Kingdom .

*Primary Examiner*—Mukund J. Shah
*Assistant Examiner*—Bruck Kifle
*Attorney, Agent, or Firm*—Michael N. Meller

[57] ABSTRACT

A process for the preparation of rufloxacin, a compound of the formula I

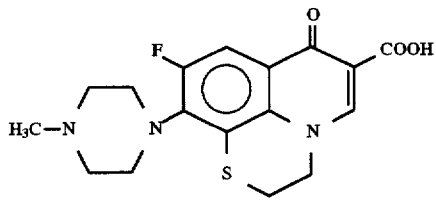

and salts thereof is described. This is effected by reducing a quinoline disulfide of formula (II) as herein defined, and subjecting the resulting 2-mercaptoethyl quinoline of formula (III) as herein defined to a cyclization in a basic medium and hydrolyzing the rufloxacin ester thus obtained and, if desired, forming the salts thereof.

9 Claims, No Drawings

PROCESS FOR THE PREPARATION OF RUFLOXACIN AND SALTS THEREOF

The present invention concerns a process for the preparation of rufloxacin and salts thereof. More particularly, the invention relates to a process for the preparation of rufloxacin hydrochloride starting from a new quinolone disulfide, to novel intermediates in such a preparation and to the hydrolysis of rufloxacin esters to rufloxacin hydrochloride.

Rufloxacin is the International Non-proprietary Name of 9-fluoro-2,3-dihydro-10-(4-methylpiperazin-1-yl)-7-oxo-7H-pyrido[1,2,3-de][1,4] benzothiazin-6-carboxylic acid of formula (I)

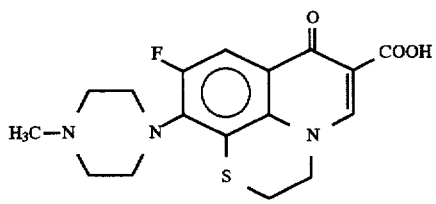

which is a quinolone antibiotic having a broad and powerful antibacterical activity on Gram-positive and Gram-negative microorganisms as well as a low toxicity and favorable pharmacokinetics.

In clinical trials rufloxacin is used in form of its hydrochloride salt; it is described by V. Cecchetti et al. in J. Med. Chem. 1987, 30, 465–473.

The most convenient method described heretofore for the preparation of rufloxacin hydrochloride is the one-pot synthesis of V. Cecchetti et al., Synthetic Communications, 1991, 21(22) 2301–2308 which, starting from ethyl 2,3,5-trifluoro-4-(4-methyl-1-piperazinyl) benzoylacetate, leads to the desired compound in a 61% total yield.

It has now been found that, starting from a quinolone disulfide, rufloxacin hydrochloride can be obtained one-pot in very high yields. Since the starting quinolone disulfide is, in its turn, obtained in high yield from an ester of 2,3,5-trifluoro-4-(4-methyl-1-piperazinyl) benzoylacetic acid, the obtention of rufloxacin hydrochloride occurs in a safer manner and in higher yields in respect of the known methods.

More particularly, it has been found that, starting from a quinolone disulfide of formula (II)

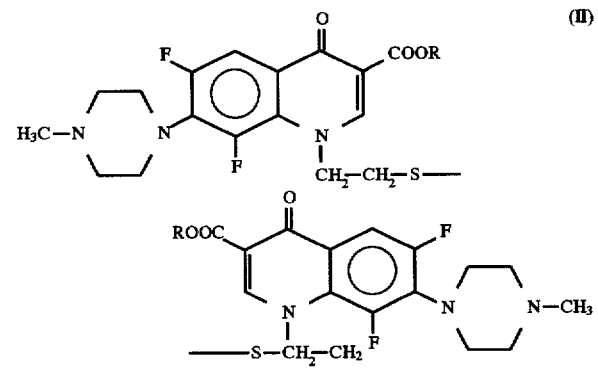

in which R represents an alkyl group of from 1 to 4 carbon atoms, more particularly methyl or, preferably, ethyl, rufloxacin hydrochloride is obtained according to the following reaction scheme:

Scheme 1

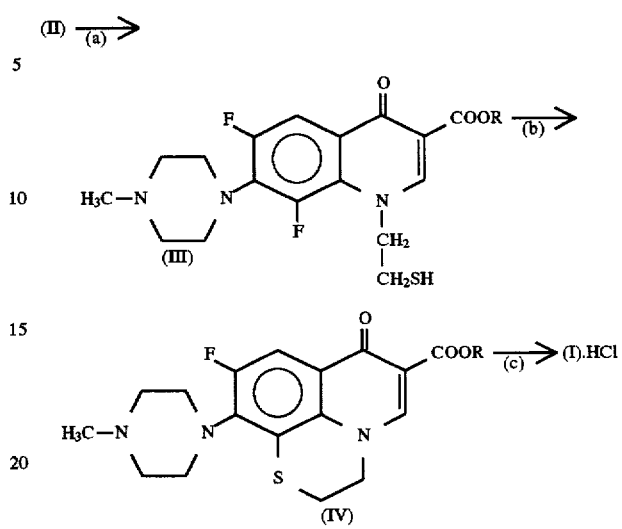

wherein R is as defined above, in a yield of at least 75%.

Thus, it is an object of the present invention to provide a process for the preparation of rufloxacin hydrochloride which comprises reacting a quinolone disulfide of formula (II), wherein R is an alkyl group of from 1 to 4 carbon atoms with a reducing agent, cyclizing the mercaptane of formula (III) with a base in an organic solvent, saponifying the rufloxacin ester of formula (IV) and isolating rufloxacin as hydrochloride.

In step (a), the reduction is carried out with a reducing agent such as sodium hydride, sodium metabisulfite, triphenylphosphine and an acid such as acetic acid or zinc and hydrochloric acid according to conventional methods.

In step (b), the cyclization is carried out with a base, such as sodium or potassium carbonate and sodium hydride, in an organic solvent, preferably N,N-dimethylformamide.

In step (c), the rufloxacin ester (IV) is subjected to a saponification, for example in acidic medium or with a base, such as sodium hydroxide as described by V. Cecchetti et al. in Chemical Communication, 1991, 21(22), 2301–2308.

More particularly, it has been found that, by treating the rufloxacin ester (IV), or a salt thereof, with hydrochloric acid, rufloxacin hydrochloride is isolated in a pure state in practically quantitative yield.

Thus, it is a further object of the present invention to provide a process for converting a rufloxacin $(C_1–C_4)$ alkyl ester into rufloxacin hydrochloride, which comprises reacting said rufloxacin ester of formula (IV), or a salt thereof, with hydrochloric acid. This hydrolysis takes place using concentrated hydrochloric acid, diluted with water or with glacial acetic acid as solvents, preferably at the boiling point of the reaction mixture, and rufloxacin hydrochloride is isolated by adding a precipitating solvent, preferably acetone. The yield is almost quantitative. After a purification with ethanol/water, the yield is from 88 to 95% of the theoretical in rufloxacin hydrochloride for pharmaceutical use.

Beside the improved yields, the acid hydrolysis of the ester according to the present invention has the advantage over the known saponification in a basic medium, of being carried out without any need of monitoring the reaction product because rufloxacin is stable in acidic medium.

The quinolone disulfide of formula (II) used as starting material for the process of the present invention is obtained in very high yields from an alkyl 2,3,5-trifluoro-4-(4-methylpiperazin-1-yl)benzoylacetate of formula (ii)

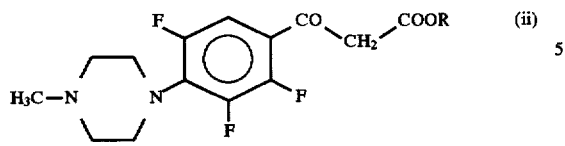

wherein R is as defined above, by reacting this compound (ii) at first with N,N-dimethylformamide dialkyl acetal of formula (iii)

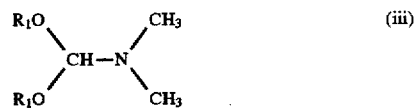

wherein $R_1$ is an alkyl of from 1 to 4 carbon atoms, in an organic solvent, then with 2-aminoethanethiol with concurrent cyclization in a basic medium and in the presence of air and isolating the disulfide (II) as such or in form of one of its salts.

The reaction of the ketoester (ii) with the acetal (iii) is carried out at a temperature of 80°+120° C. in an organic solvent, such as in toluene with reflux. At the end of the reaction, the solvent is totally or partially eliminated and the residue is immediately treated with 2-aminoethanethiol, preferably as a salt such as the hydrochloride, in the presence of a base. This reaction is carried out in water, optionally in admixture with an organic solvent which may be the same as that of the precedent reaction, or even different, for example ethyl acetate or toluene. Cyclization takes place by treatment with a base at a temperature of 20°+30 C. The base used may be organic such as, for example, trimethylamine, triethylamine or diazabicyclooctane, or inorganic, such as, for example, sodium or potassium hydroxide, sodium or potassium carbonate, sodium hydride, sodium or potassium acetate. The reaction is carried out in the presence of air. The formation of the disulfide is complete after a 10+15-hour stirring.

The quinolone disulfide (II) may be isolated according to known methods, particularly by eliminating the salts, evaporating the solvent and taking up the residue with a solvent in which the product crystallizes, for example acetone. It may also be recrystallized from a mixture of methanol/water (3:1 v/v).

The compound thus obtained of formula (II) may be isolated as a salt thereof or the raw free base may be transformed into one of its acid addition salts, for example with hydrochloric, hydrobromic, sulfuric, methanesulfonic, fumaric, maleic, oxalic acid.

The ketoester (ii) used as starting material is known from the literature when R is ethyl. It may be prepared according to known methods (Chem. Pharm. Bull. 1986, 34, 4098–4102) from 2,3,4,5-tetrafluorobenzoic acid of formula (i)

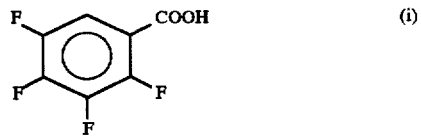

by reaction of its acid chloride (obtained with thionyl chloride in N,N-dimethylformamide) with a dialkyl malonate of formula ROOC—$CH_2$—COOR, wherein R is as defined above, in the presence of a magnesium alcoholate, for example the ethylate, and by subsequent reaction of the compound (iv)

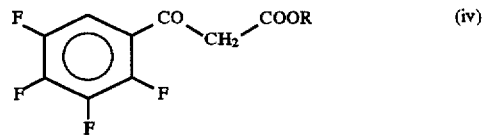

even without isolating it, with N-methylpiperazine.

The process of the present invention may be carried out without isolating the intermediates. Moreover, not only the steps (a)–(c) of Scheme 1 may take place without isolation of the compounds (III) and (IV), but also the reactions which lead to the quinolone disulfide (II) may be carried out in one-pot. Thus, the whole processing (i)→(ii)→(II)→(III)→(IV)→(I) may be conducted without isolating the intermediate products or by isolating compounds (ii) and (II) only, without purifying them.

Furthermore, the yields obtained according to the process of the present invention, even taking into account the whole processing (i)→(I), are very good. Thus, the yields in the sequence (ii)→(II) may be of 80% or more, while in the reaction sequence (II)→(I) the yields may be at least 85%. If the whole processing (i)→(I) is carried out without purifying anyone of the intermediate compounds, rufloxacin hydrochloride may be obtained in a global yield of 70% or more.

Finally, the process of the present invention allows the preparation of rufloxacin hydrochloride by using a quinolone disulfide (II) which is stable and thus avoids the sensitive intermediates described by V. Cecchetti et al. in Synthetic Communications, 1991, 21(22), 2301–2308.

The mercaptoethyl quinolone of formula (III) is a novel compound and is a further object of the present invention. It may be isolated and characterized but it is more suitable to cyclize it "in situ" according to step (b) of the process of the present invention.

The following examples illustrate the invention without, however, limiting it.

PREPARATIONS

I. Manufacture of a Quinolone Disulfide of Formula (II)

(a) A mixture of 80 g of ethyl 2,3,5-trifluoro-4-(4-methylpiperazin-1-yl)benzoylacetate (ii, R=$C_2H_5$) and 45 g of N,N-dimethylformamide dimethyl acetal (iii, $R_1$=$CH_3$) in 250 ml of toluene is heated at reflux, then the solvent is distilled off to reach 110° C. and a further amount of toluene is added thereinto to about the initial volume. The solution thus obtained is washed twice with water, then 40 ml of water and 30 g of 2-aminoethanethiol hydrochloride are added thereinto and 25 ml of 30% sodium hydroxide are added dropwise, in 30 minutes, to the reaction mixture. Such a mixture is stirred 2 hours at room temperature (20°+30 C.), then the aqueous phase is eliminated and the organic phase is washed with water, dried and concentrated under vacuum to dryness. The residue is taken up with 700 ml of ethyl acetate and 50 g of micronized potassium carbonate are added to the solution. The mixture is stirred for 15 hours in the presence of air, then it is heated 2 hours at reflux. After having filtered the salts off, the solution is concentrated under vacuum, the residue is taken up with ethyl acetate and filtered. Thus, 80 g of bis-[2-[(6,8-difluoro-3-ethoxycarbonyl-4-oxo-7-(4-methylpiperazin-1-yl)-1,4-dihydroquinolin-1-yl]]ethyldisulfide (II, R=$C_2H_5$) are obtained.

$^1$H-NMR (300 mHz, $CDCl_3$): 1.41 (t, 3H, $CH_3$—$CH_2$, J=7 cps); 2.36 (s, 3H, N—$CH_3$); 2.56 (m, 4H, piperazine);

3.10 (t, 2H, CH$_2$—S); 3.36 (m, 4H, piperazine); 4.39 (q, 2H, CH$_3$—$\underline{CH_2}$, J=7 cps); 4.51 (m, 2H, CH$_2$—N); 7.97 (dd, 1H, aromatic, J$_{HF}$=2 cps, 12 cps); 8.34 (s, 1H, =CH).

(b) A mixture of 52.8 g of ethyl 2,3,5-trifluoro-4-(4-methylpiperazin-1-yl)benzoylacetate, 20 g of N,N-dimethylformamide dimethyl acetal and 165 ml of N,N-dimethylformamide is heated at 100°+105 C. for 1 hour. To the solution 26 ml of water, 18.7 g of 2-aminoethanethiol hydrochloride are added thereinto, and successively in 30 minutes 32.8 ml of 30% sodium hydroxide. The reaction mixture is stirred 1 hour at 20°+25 C., then poured into 450 ml ice-water and extracted with 350 ml of ethyl acetate. The organic phase is washed with water, dried and treated with 33 g of potassium carbonate. The suspension is stirred in the presence of air for 20 hours. After filtration, the solution is concentrated under vacuum to a small volume. The crystalline product is filtered and 55.7 g of the quinolone disulfide are obtained. Yield: 88.6%.

(c) A mixture of 40 g of ethyl 2,3,5-trifluoro-4-(4-methylpiperazin-1-yl)benzoylacetate, 22.5 g of N,N-dimethylformamide dimethyl acetal and 125 ml of benzene is heated at reflux for 2 hours. The solvent is distilled off and a further volume of benzene is added. To the solution thus obtained 20 ml of water and 22 g of 2-aminoethanethiol hydrochloride are added thereinto, and successively in 1 hour 32 ml of 30% sodium hydroxide. After stirring 2 hours at room temperature, the organic phase is separated, washed with water, dried and concentrated under vacuum to dryness. The residue is extracted with 280 ml of ethyl acetate and treated with 27.5 g of micronized potassium carbonate. The suspension is stirred for 15 hours in the presence of air, then heated 2 hours at reflux. After filtration of the salts, the solution is concentrated under vacuum and the residue is crystallized from ethyl acetate to give 45.7 g of quinolone disulfide (II, R=C$_2$H$_5$). Yield: 96%.

(d) A mixture of 60 g of ethyl 2,3,5-trifluoro-4-(4-methylpiperazin-1-yl)benzoylacetate, 35 ml of N,N-dimethylformamide dimethyl acetal and 220 ml of toluene is heated at reflux for 1 hour. The solvent is distilled off and a further volume of toluene is added. The solution is cooled to 20° C., washed with water and successively 60 ml of water, 23 g of 2-aminoethanethiol hydrochloride and 31 g of sodium acetate trihydrate are added. After stirring 2 hours at room temperature the organic phase is separated, washed with water, dried and concentrated under vacuum to dryness. The residue is treated with 600 ml of acetonitrile and 60 g of micronized anhydrous potassium carbonate are added. The suspension is stirred for 10 hours in the presence of air, then heated for 90 minutes at reflux. After filtration of the salts, the solution is concentrated under vacuum to dryness. The residue is treated with water and filtered to give 58.8 g of quinolone disulfide.

II. Preparation of a quinolone disulfide (II) starting from 2,3,4,5-tetrafluorobenzoic acid (a) Ethyl 2,3,5-trifluoro-4-(4-methylpiperazin-1-yl) benzoylacetate (ii, R=C$_2$H$_5$)

A suspension of 200 g of 2,3,4,5-tetrafluorobenzoic acid, 225 ml of thionyl chloride and 5 ml of N,N-dimethylformamide, prepared at 20° C., is heated at reflux for 3 hours. After cooling at 40° C., the thionyl chloride in excess is evaporated off under vacuum. The residue is taken up with toluene and the solution is concentrated again at 40° C. under vacuum. Thus 219 g of raw 2,3,4,5-tetrafluorobenzoyl chloride are obtained as a yellowish oil. A mixture of 1200 ml of toluene, 220 g of diethyl malonate and 153 g of magnesium ethylate, prepared at 20° C., is heated one hour at reflux, then it is cooled to 5° C. and the acid chloride above obtained is added thereto, by keeping the temperature below 10° C. After a 30-minutes stirring, the mixture is made acid with concentrated hydrochloric acid and the two phases are separated. The organic phase is diluted with water, made acid with sulfuric acid to pH 1.0 and heated at reflux for 7 hours, namely until the reaction is over. The mixture is cooled, the aqueous phase is separated and the organic one is taken up with water and made basic with sodium hydroxide to a very basic pH value. The aqueous phase is separated and the organic one is again extracted with water. The combined aqueous phases are made acid with concentrated hyarochloric acid to pH 1 and extracted twice with toluene. The toluene phase is concentrated under vacuum, the residue is taken up with 1250 ml of acetonitrile. To this mixture, at first 80 g of sodium bicarbonate and then 110 ml of N-methylpiperazine are added and the reaction mixture is heated 3 hours at reflux. By dilution with water the desired product precipitates and it is then filtered and washed with water. The wet product thus obtained is suspended in toluene and the suspension is evaporated by distillation until the solution becomes anhydrous. This solution contains 0.89 mole of ethyl 2,3,5-trifluoro-4-(4-methylpiperazin-1-yl)benzoylacetate and is directly used for the subsequent step (b).

(b) Bis[2-[(6,8-difluoro-3-ethoxycarbonyl-4-oxo-7-(4-methylpiperazin-1-yl)-1,4-dihydroquinolin-1-yl]] ethyldisulfide (II, R=C$_2$H$_5$)

To the toluene solution of ethyl 2,3,5-trifluoro-4-(4-methylpiperazin-1-yl)benzoylacetate (ii, R=C$_2$H$_5$) previously obtained, 173 ml of N,N-dimethylformamide dimethyl acetal (iii, R$_1$=CH$_3$) are added, then the solution is treated as described in PREPARATION (I) to obtain 333.4 g of the quinolone disulfide.

The global yield starting from 2,3,4,5-tetrafluorobenzoic acid is 78.8%.

III. By operating as described in PREPARATION II, but carrying out step (b) according to the teaching of PREPARATION I(c), the global yield of quinolone disulfide is 90.5%.

EXAMPLE 1

(a) A solution of 11.2 g of disulfide, obtained in PREPARATION I, in methylene chloride containing 10.5 g of triphenylphosphine and few drops of glacial acetic acid is maintained under agitation for 20 hours. After this time the disulfide is solubilized; the solution is concentrated under vacuum and the residue is treated with 80 ml of N,N-dimethylformamide, 10 g of potassium carbonate, then stirred for 20 hours at room temperature. The reaction mixture is diluted with water and the product is filtered, washed with acetone and dried. Thus 10.1 g of rufloxacin ethyl ester are obtained. Yield: 94%.

(b) A solution of 10 g of rufloxacin ethyl ester, obtained in step (a), in 30 ml of glacial acetic acid and 10 ml of concentrated hydrochloric acid is refluxed for 2 hours. After dilution with 100 ml of acetone the precipitated product is washed with filtered hot ethanol/water. Thus 9.28 g of pure rufloxacin hydrochloride are obtained. Yield: 92%.

EXAMPLE 2

(a) To a suspension of 0.8 g of sodium hydride (60% in oil) in 10 ml of N,N-dimethylformamide is slowly added a solution of 8.2 g of quinolone disulfide (II, R=C$_2$H$_5$) in 40 ml of N,N-dimethylformamide. The reaction mixture is stirred at room temperature for 1 hour, treated with a Mixture of methanol/water/acetic acid (1:1:1 v/v/v) and then poured into 50 ml of ice-water. The crystalline product is collected by filtration, washed with water and acetone to give 7.75 g of rufloxacin ethyl ester.

(b) A solution of 10 g of rufloxacin ethyl ester in 30 ml of acetic acid and 10 ml of 35% hydrochloric acid is refluxed for 2 hours. To the collected solution 135 ml of acetone are added and the separated product is collected by filtration. The wet residue is suspended in a mixture ethanol/water, heated at 55°+60° C. for 15 minutes and filtered. Thus 9.8 g of pure rufloxacin hydrochloride are obtained.

EXAMPLE 3

To a suspension of 1.5 g of sodium hydride (60% in oil) in 10 ml of N,N-dimethylformamide is added dropwise a solution of 15 g of quinolone disulfide (II, R=$C_2H_5$) in 60 ml of N,N-dimethylformamide in 5 hours, under stirring at 25° C. The stirring is continued for 2 hours. The reaction mixture is treated with a solution of methanol/water/acetic acid (1:1:1 v/v/v), then is diluted with 70 ml of water. The crystalline product is collected by filtration, washed with water and acetone to give 12 g of rufloxacin ethyl ester.

EXAMPLE 4

(a) To a suspension of 1.25 g of sodium hydride (60% in oil) in 15 ml of N,N-dimethylacetamide is slowly added a solution of 12.5 g of quinolone disulfide (II, R=$C_2H_5$) in 65 ml of N,N-dimethylacetamide. The reaction mixture is stirred at 20°+25° C. for 2 hours, then poured into 50 ml of a mixture of methanol/water/acetic acid (1:10:2 v/v/v). The wet product is filtered and used in the subsequent step.

(b) A solution of wet product, obtained in step (a), in 30 ml of 15% hydrochloric acid is refluxed until a solution is obtained. The ethanol is removed by azeotropical distillation and the residual solution is concentrated under vacuum. The wet residue is suspended in 60 ml of acetone and refluxed for 30 minutes. The cooled suspension is filtered to give 11.1 g of pure rufloxacin hydrochloride.

EXAMPLE 5

To a solution of 4 g of quinolone disulfide (II, R=$C_2H_5$) in a mixture of 50 ml of methanol, 10 ml of water and 1.5 ml of acetic acid, 3 g of triphenylphosphine are added. The reaction mixture is stirred at 20°+25° C. for 2 hours. After removal of the residue by filtration, the solution is concentrated under vacuum. 50 ml of N,N-dimethylformamide are added to the residue and the solution obtained is concentrated to a small volume. The solution is treated with 4.2 g of potassium carbonate, stirred at 30°+35° C. for 1 hour and poured into 120 ml of water. The crystalline product is collected by filtration, washed with water and acetone to give 3.05 g of rufloxacin ethyl ester.

EXAMPLE 6

(a) To a mixture of 55 ml of water, 220 ml of methanol and 5.5 ml of acetic acid, 15.4 g of quinolone disulfide (II, R=$C_2H_5$) are added.

The solution thus obtained is treated with 11 g of triphenylphosphine and stirred at 20°+25° C. for 2 hours. At the end of the reaction, the solution is concentrated under vacuum to dryness. The residue is crystallized from ethanol/isopropyl ether. Thus, 11.2 g of mercaptoethyl quinolone (III, R=$C_2H_5$) are obtained.

$^1$H-NMR (300 mHz, $CDCl_3$): 1.40 (t, 3H, C$\underline{H}_3$—CH$_2$, J=7 cps); 2.36 (s, 3H, N—CH$_3$); 2.55 (m, 5H, piperazine+SH); 2.97 (m, 2H, C$\underline{H}_2$—S); 3.35 (bs, 4H, piperazine); 4.3+4.5 (m, 4H, CH$_3$—C$\underline{H}_2$+C$\underline{H}_2$—N); 7.94 (dd, 1H, aromatic, J$_{HF}$=2 cps, 12 cps); 8.38 (s, 1H, =CH).

(b) To a solution of 10.5 g of mercaptoethyl quinolone in 65 ml of N,N-dimethylformamide, 13.2 g of potassium carbonate are added. The reaction mixture is stirred at 30°+35 C. for 1 hour. By dilution with 150 ml of water the product is filtered and washed with water. Thus, 8.5 g of rufloxacin ethyl ester are obtained. Yield: 85%.

EXAMPLE 7

(a) A mixture of 155 g of diethyl malonate, 107 g of magnesium ethylate and 800 ml of toluene is refluxed for 1 hour, then it is cooled to 5° C. and 153 g of 2,3,4,5-tetrafluorobenzoyl chloride (obtained from 140 g of 2,3,4,5-tetrafluorobenzoic acid) are added thereto, by keeping the temperature below 10° C. After a 45-minutes stirring the mixture is acidified with diluted sulfuric acid and the two phases are separated. The organic phase is treated with 150 ml of water, acidified to pH 1.0 with diluted sulfuric acid and refluxed for 8 hours. After cooling the mixture, the aqueous phase is separated and the organic one is treated with water and sodium hydroxide to a very basic pH value. The aqueous phase is separated and the organic one is extracted with water. The combined aqueous phases are acidified with concentrated hydrochloric acid to pH 1 and extracted twice with toluene. The toluene phase is concentrated under vacuum and the residue is taken up with 880 ml of acetonitrile. To this solution, at first 56 g of sodium carbonate and then 77 ml of N-methylpiperazine are added and the reaction mixture is heated 4 hours at reflux. The product precipitates by dilution with water, then is filtered and washed with water. The wet product is taken up with 350 ml of toluene and the solution is evaporeted until it becomes anhydrous. This solution contains 0.635 mole of ethyl 2,3,5-trifluoro-4-(4-methylpiperazin-1-yl)benzoylacetate.

(b) To the solution obtained in step (a), 121 g of N,N-dimethylformamide dimethyl acetal are added and the mixture is heated at reflux for 2 hours. The solvent is distilled off and a further volume of toluene is added. To the solution thus obtained 110 ml of water and 119 g of 2-aminoethanethiol hydrochloride are added thereto and successively, in 1 hour, 170 ml of 30% sodium hydroxide. After stirring 2 hours at room temperature, the organic phase is separated, washed with water, dried and concentrated under vacuum to dryness. The residue is extracted with 1500 ml of ethyl acetate and the solution is treated with 148.5 g of micronized potassium carbonate. The suspension is stirred for 18 hours in the presence of air, then refluxed for 2 hours. After filtration of the salts, the solution is concentrated under vacuum and the residue is the crude quinolone disulfide (II, R=$C_2H_5$).

(c) The crude quinolone disulfide (255 g) obtained in step (b) is treated with 1200 ml of N,N-dimethylacetamide. To the solution thus obtained, a suspension of 24.6 g of sodium hydride (60% in oil) in 300 ml of N,N-dimethylacetamide is added. The reaction mixture is stirred at 20°+25° C. for 2 hours, then poured into 950 ml of a mixture of methanol/water/acetic acid (1:10:2 v/v/v). The wet product is the crude rufloxacin ethyl ester used in the subsequent step.

(d) A solution of wet product, obtained in step (c), in 600 ml of 15% hydrochloric acid is refluxed until a solution is obtained. The ethanol is removed by azeotropical distillation and the residual solution is concentrated under vacuum. The residue is treated with 1150 ml of acetone and refluxed for 30 minutes. The cooled suspension is filtered to give 219 g of pure rufloxacin hydrochloride.

The global yield starting from 2,3,4,5-tetrafluorobenzoic acid is 76%.

I claim:

1. A process for the preparation of rufloxacin of formula (I)

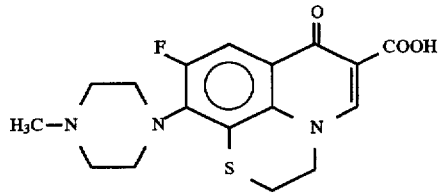

which comprises (a) reducing a quinolone disulfide of formula (II)

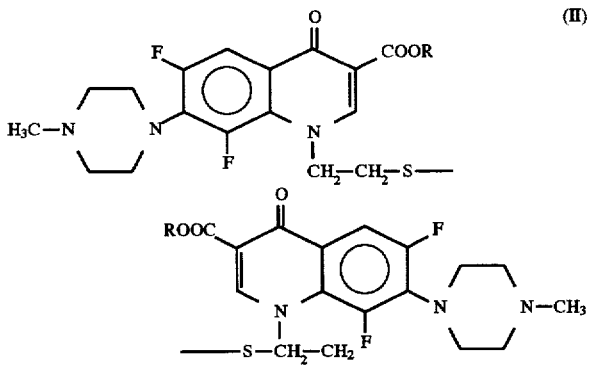

in which R is an alkyl group of from 1 to 4 carbon atoms, or a salt thereof;

(b) subjecting the 2-mercaptoethyl quinolone thus obtained of formula (III)

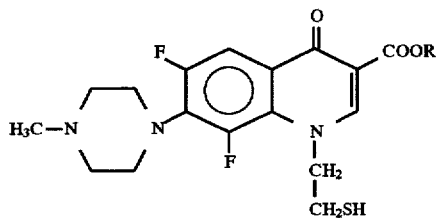

in which R is as defined above, to a cyclization in a basic medium in an organic solvent;

(c) hydrolyzing the rufloxacin ester thus obtained of formula (IV)

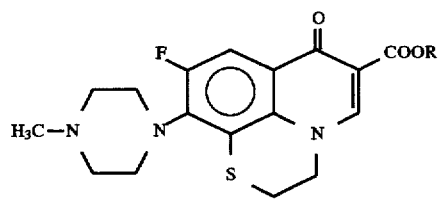

wherein R is as defined above, in an acidic or basic medium.

2. A process according to claim 1, in which the steps (a), (b) and (c) are carried out without isolating the intermediate compounds (III) and (IV).

3. A process according to claim 1, in which step (c) is carried out with hydrochloric acid.

4. A process according to claim 3 in which glacial acetic acid is used as a solvent.

5. A process according to claim 3 in which the end product is isolated by addition of acetone.

6. A process according to claim 1 in which a quinolone disulfide of formula (II) in which R is ethyl, is used as starting material.

7. A process for the preparation of rufloxacin hydrochloride of formula (V)

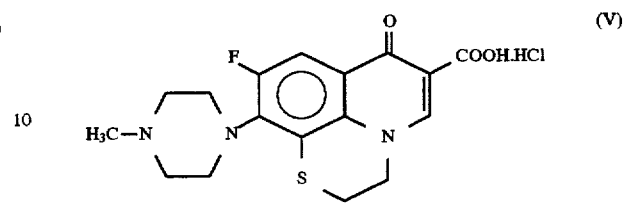

which comprises (a) reducing a quinolone disulfide of formula (II)

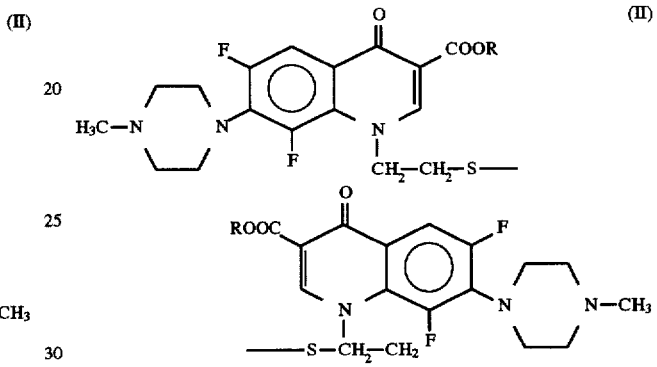

in which R is an alkyl group of from 1 to 4 carbon atoms, or a salt thereof;

(b) subjecting the 2-mercaptoethyl quinolone thus obtained of formula (III)

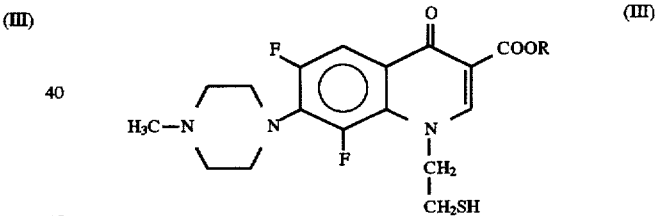

in which R is as defined above, to a cyclization in a basic medium in an organic solvent;

(c) hydrolyzing the rufloxacin ester thus obtained of formula (IV)

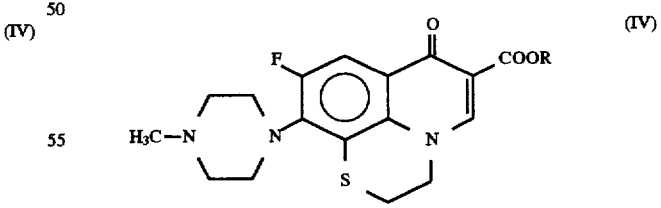

wherein R is as defined above, in a acidic or basic medium;

(d) hydrolyzing said rufloxacin ester of formula (IV) in which R is as defined above, with hydrochloric acid.

8. A process according to claim 7, in which concentrated hydrochloric acid, diluted with water or with glacial acetic acid as solvents, is used as hydrolyzing agent.

9. A process as claimed in claim 7 in which rufloxacin hydrochloride is recovered by addition of acetone.

* * * * *